United States Patent [19]

Alcidi et al.

[11] Patent Number: 5,701,906
[45] Date of Patent: Dec. 30, 1997

[54] METHOD AND APPARATUS FOR ACQUIRING AND PROCESSING ELECTROCARDIOGRAPHIC SIGNALS

[75] Inventors: Paolo Alcidi, Via Gustavo Console 8, 50141 Firenze; Gino Grassi, Via Pasqui giá Via degli Orti 31, 50019 Sesto Fiorentino, both of Italy

[73] Assignees: Paolo Alcidi, Florence; Gino Grassi, Sesto Fiorentino, both of Italy; a part interest

[21] Appl. No.: 651,697

[22] Filed: May 21, 1996

[30] Foreign Application Priority Data

May 22, 1995 [IT] Italy ................................. FI91A0111

[51] Int. Cl.$^6$ ................................................ A61B 5/0402
[52] U.S. Cl. ................................................ 128/696
[58] Field of Search ........................... 128/696, 699, 128/703, 704

[56] References Cited

U.S. PATENT DOCUMENTS

| | | | |
|---|---|---|---|
| 5,458,122 | 10/1995 | Hethuin | 128/696 |
| 5,555,888 | 9/1996 | Brewer et al. | 128/702 |

*Primary Examiner*—Scott Getzow
*Attorney, Agent, or Firm*—McGlew & Tuttle

[57] ABSTRACT

Method and apparatus for acquiring and processing electrocardiographic signals comprising the steps of detecting and recording a first basic electrocardiographic waveform of a subject tested under relaxed condition, i.e at rest, and a second electrocardiographic waveform of the same subject tested at the end of an induced stress, which method further comprises comparing the said basic waveform with the second waveform and detecting, from the thus operated comparison, the instant in which a change in the second waveform takes place, by evaluating the time elapsed from a preset initial instant. (FIG. 1).

10 Claims, 5 Drawing Sheets

METHOD AND APPARATUS FOR ACQUIRING AND PROCESSING ELECTROCARDIOGRAPHIC SIGNALS

FIELD OF THE INVENTION

The present invention relates to a method and an apparatus for the acquisition and processing of electrocardiographic signals.

BACKGROUND OF THE INVENTION

It is known that the electrocardiographic signals recorded by an electrocardiograph connected on two points of the human body derive from the extracellular current of the heart cells upon the depolarization/repolarization of the same cells: said current giving rise, upon the myocardium depolarization, to the formation of the electrocardiographic complex known as QRS and, upon the respective repolarization stage, to the corresponding electrocardiographic S–T segment and T wave. It is also known that, during each cardiac cycle, the intensity of said extracellular current depends on the different electrical behaviour between the cardiac mass being depolarized and the one still polarized. In a healthy heart, when the myocardium cells are either all polarized or all depolarized, the current intensity is approximately equal to zero and the relevant electrocardiographic tracing lies on a baseline.

Using only the currently known electrocardiographic apparatuses it is impossible, to detect and analyse the ischemic area of the myocardium.

SUMMARY AND OBJECTS OF THE INVENTION

The main object of the present invention is to overcome the above mentioned drawback by providing a method and an apparatus for processing the electrocardiographic signals, which allow one to detect and locate, in a non invasive way, and at reduced cost, the ischemic areas of the left ventricle's tissue.

In the method of the present invention, a first basic electrocardiographic waveform is detected and reported from the subject in a relaxed condition. A second electrocardiographic waveform is also detected and recorded from the subject at the end of an induced stress. The first and second electrocardiographic waveforms are compared and a point in time when the second waveform differs from the first waveform is determined.

The apparatus for implementing this method, includes ECG differential amplifier means connectable to a thorax of the subject. A filter means receives signals from the differential amplifier means. The filter means includes a first filter which is a high pass filter for stabilization of a base line of the electrocardiographic waveform. The filter means also includes a second filter which is a low pass filter for minimizing accidental noises due to muscular tremor. After the filter means, an analogue-digital converter means digitally converts the electrocardiographic waveform. An averaging pre-processor means then forms an average basic QRS with an ascending segment QR and a descending segment RS. A programmable microprocessor located downstream of the averaging pre-processor means performs the operations of detecting a first normalization factor of the RS segment and detects a second normalization factor of the QR segment. The microprocessor then normalizes the RS and QR segments and connects the normalized QR and RS segments to attain a corresponding averaged QRS bilaterally normalized. The normalized average QRS is aligned with another averaged QRS and the difference between the two is detected. A display means then displays signals or wave forms from the programmable microprocessor means.

The advantages deriving from the present invention lie essentially in that it is possible to search and locate the ischemic areas of the myocardium through a bloodless, cost-effective procedure which is relatively simple to carry out while being accurate and reliable at the same time; that an apparatus according to the invention may be easily set up and used both within a hospital and in outpatient departments, and is of relatively low cost.

These and other advantages and characteristics of the invention will be best understood by anyone skilled in the art from a reading of the following description in conjunction with the attached drawings given as a practical exemplification of the invention, but not to be considered in a limitative sense.

DETAILED DESCRIPTION OF THE PREFERRED EMBODIMENT

Figure 1:
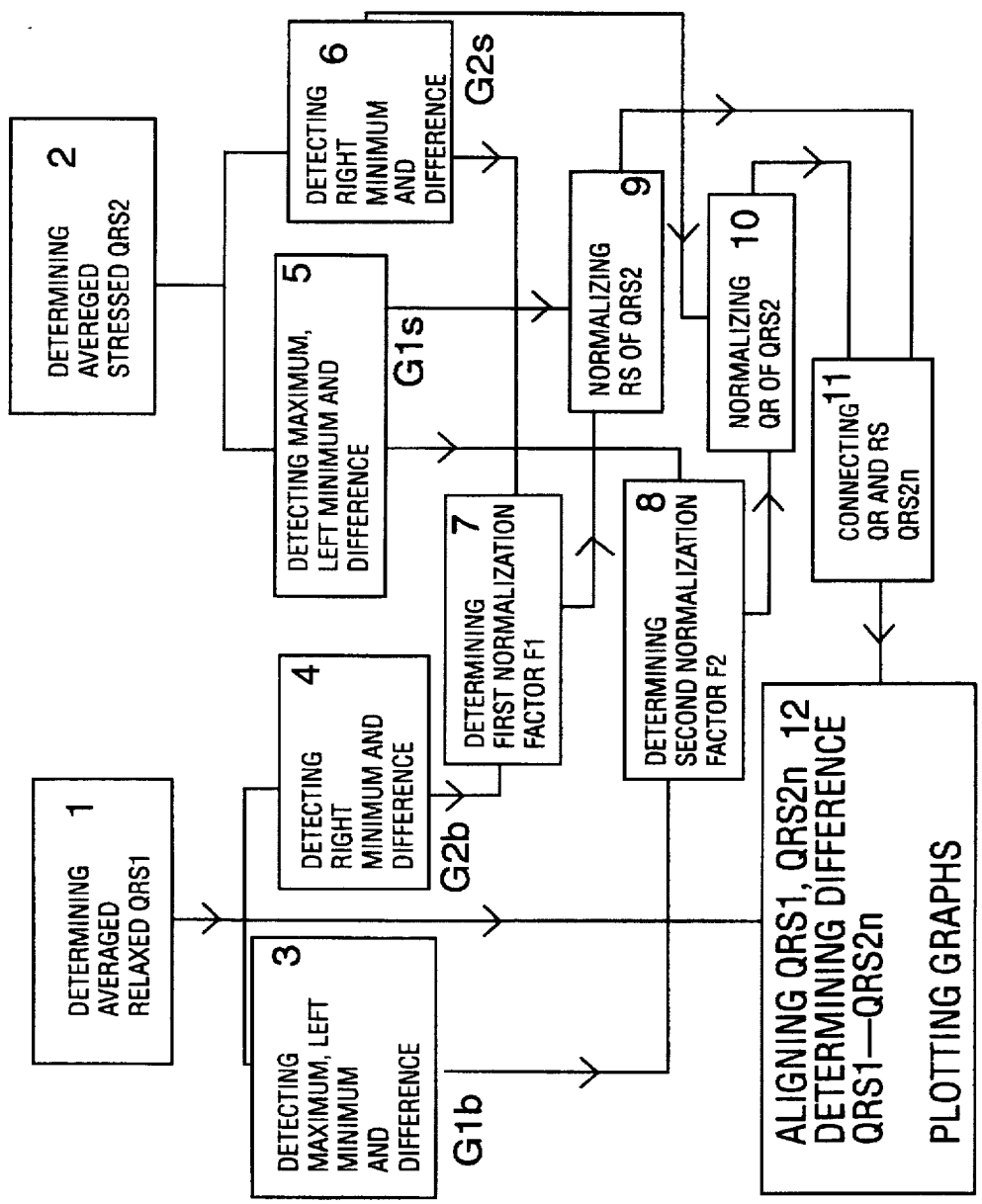
FIG. 1 is a block diagram showing the various steps of the operating method according to the invention.

Reduced to its basic structure, and reference being made to the figures of the attached drawings, a method of acquiring and processing electrocardiographic signals, particularly for analyzing and localising ischemic areas of the left ventricle's tissue, comprises, essentially, comparing the waveform of a suitably averaged and normalized basic QRS, the latter being acquired from electrocardiographic analysis of a patient at rest, with a QRS waveform being averaged and normalized with respect to the first one, and which is recorded during an induced ischemia (for example by stress or administration of pharmacologic substances) in the same patient. The subsequent comparison of the two QRS complexes allows detecting the instant in which a change takes place in the ischemic QRS waveform, starting from the start of the relevant depolarization cycle. Then, the ischemic area of the myocardium is localized.

Advantageously, according to the invention and reference being made to the attached drawings, the operating method according to the invention comprises detecting and recording a first electrocardiographic waveform of a subject in relaxed condition, i.e at rest, and a second electrocardiographic waveform of the same subject at the end of an induced stress, and further comprises:

determining the averaged basic QRS from the first electrocardiographic tracing acquired under relaxed condition of the patient, i.e. at rest (QRS1) (block 1);

determining the averaged QRS of the second electrocardiographic waveform acquired at the end of an induced stress (QRS2) (block 2). Such operations must be carried out, according to a so-called averaging technique known per se to those skilled in the art, on corresponding samples of, for example, 40 heartbeats;

detecting the maximum (R1) of said first averaged QRS (QRS1), and the minimum (Q1) at the left side of the maximum (R1) and determining the difference between them (G1b=R1−Q1) (block 3);

detecting the minimum (S1) of said first averaged QRS (QRS1) at the right side of the respective maximum (R1) and determining the difference between them (G2b=R1−S1) (block 4);

detecting the maximum (R2) of said second averaged QRS (QRS2), and the minimum (Q2) at the left side of the maximum and determining the difference between them (G1s=R2−Q2) (block 4);

detecting the minimum (S2) of said second averaged QRS (QRS2) at the right side of the respective maximum (Q2) and determining the difference between them (G2s=R2−S2) (block 5);

determining a first normalization factor (f1) of the RS segment and a second normalization factor (f2) of the QR segment, for the normalization of the second averaged QRS (QRS2), said first normalization factor being determined by the ratio between the difference G2b and the difference G2s, and the second normalization factor being determined by the ratio between the difference G1b and the difference G1s (blocks 7 and 8);

carrying out the normalization of the segment RS of said second averaged QRS (QRS2) by the said first normalization factor (f1) (block 9);

carrying out the normalization of the segment QR of said second averaged QRS (QRS2) by the said second normalization factor (f2) (block 10);

connecting the two thus normalized segments QR and RS of the second averaged QRS so as to attain a corresponding avereaged QRS bilaterally normalized (QRS2n) (block 11);

aligning, that is overlapping said normalized averaged QRS (QRS2n) with said first averaged QRS by evaluating the difference between them and plotting the respective graphs (block 12). The normalization step is operated by taking into account a "diastolic current" offset—and compensating the negative effects thereof on the measurement being carried out—which offset should be associated to the ischemic QRS during the process of depolarization of the cells of the cardiac ventricular mass, until the mass of the ischemic cells results involved in the same process, inasmuch as, at the end of the depolarization of the ischemic cells, the diastolic current is cancelled and a sistolic current, which is quite different from the diastolic one, may be generated. Accordingly, since the moment at which the ischemic cells will become depolarized cannot be known in advance, a proper normalization is operated, according to the invention, by carrying out the above said bilateral normalization of the ischemic QRS, which takes into account the offset due to both the diastolic and sistolic current. In fact, at the beginning of the depolarization cycle, if a current is present, this cannot be but a diastolic one, while at the end of the cycle, any current being present is a sistolic current, thereby allowing a comparison between the basic QRS and the ischemic QRS, which represent signals of different nature, without knowing in advance the instant at which a difference in the electrical behaviour of the cells of the cardiac ventricular mass will be generated.

It is understood that the selection of the points of minimum of said QRS is not binding over the determination of normalization factors, since other characteristics points of the curves can be selected, even in a number greater than two, such as points at which the local tangent exceeds a preset threshold.

Advantageously, according to the invention, at least a first and a second basic mean QRS waveforms are determined to allow for a check comparison between them and to leave out errors of measurement. This operation will be described in detail later on.

Figure 3:
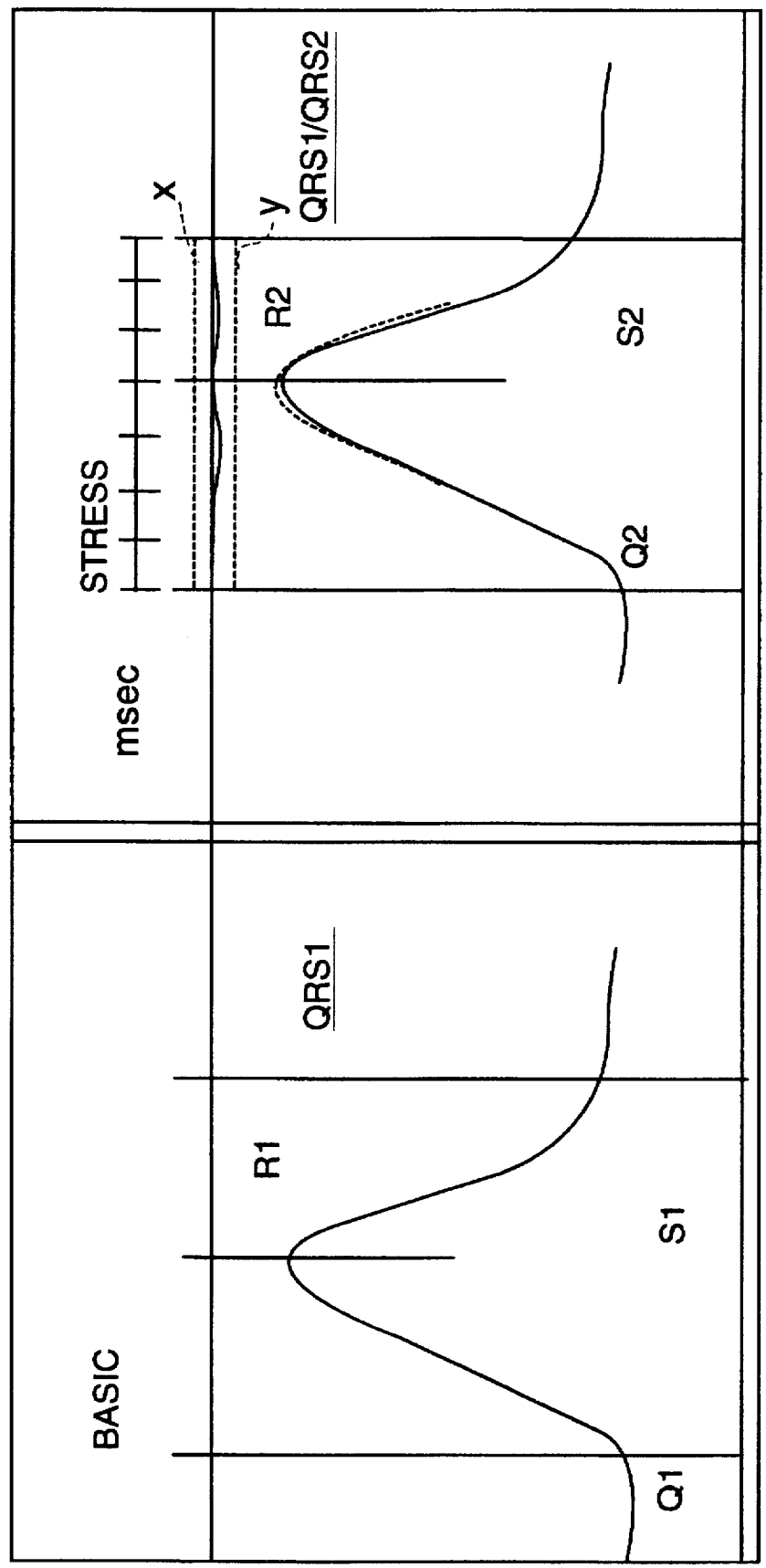
FIG. 3 is a series of four graphs showing the result of a test carried out on a healthy patient, according to a method of the invention.
Figure 4:
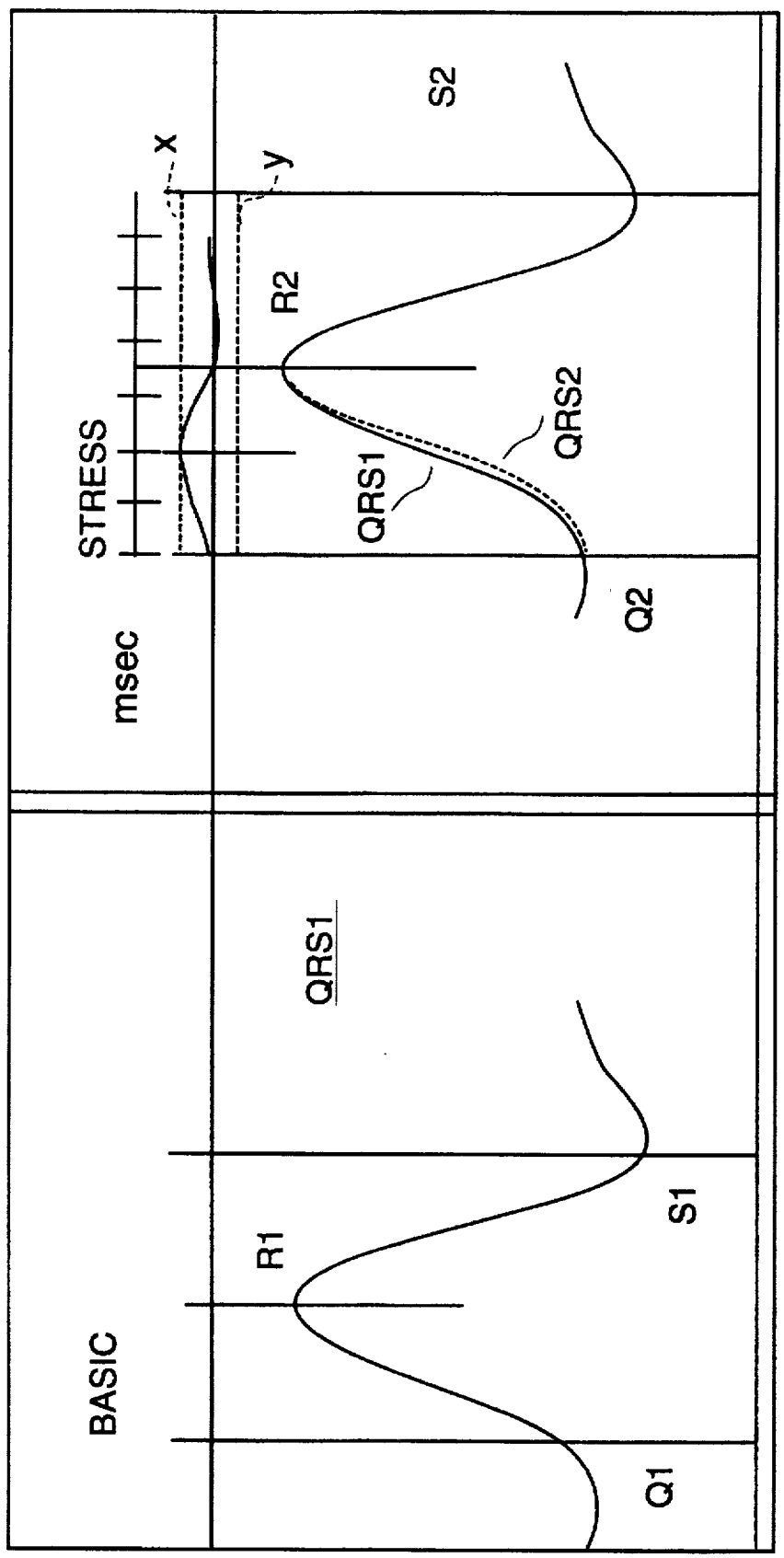
FIG. 4 is a series of four graphs showing the result of a test carried out on a patient suffering from inferior apical ischemia, according to a method of the present invention.
Figure 5:
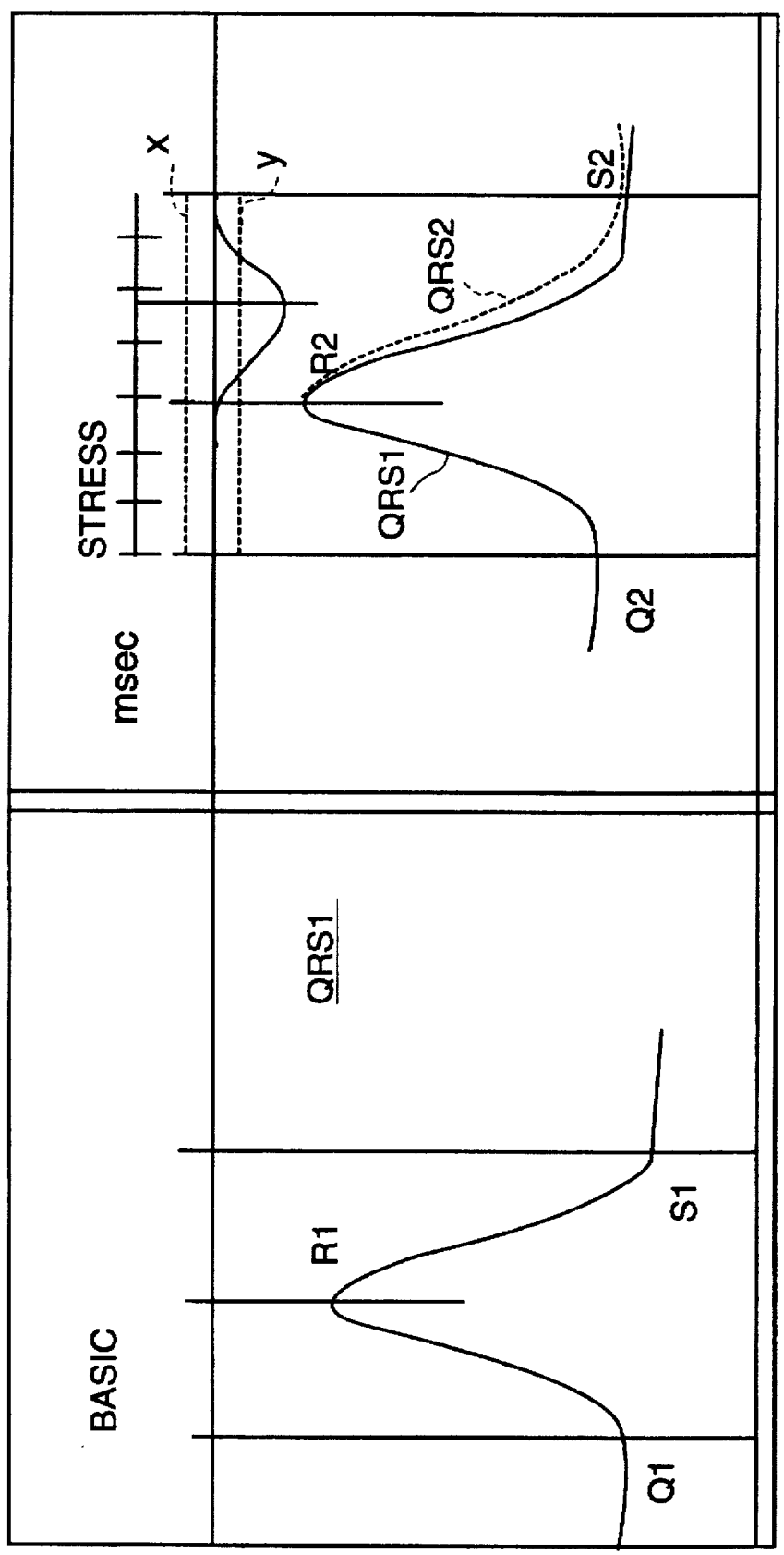
FIG. 5 is a series of four graphs showing the result of a test carried out on a patient suffering from lateral ischemia, according to a method of the present invention.

Since in the ischemic QRS, being normalized according to the above described operating procedure, the effects of the diastolic and sistolic currents are eliminated or at least minimized and, besides, the amplitude of such QRS is made equal to that of the corresponding basic QRS, the instantaneous variations of the shape of the final ischemic QRS complex with respect to that of the basic QRS are exclusively attributable to corresponding electrical variations of the ischemic mass of the myocardium. Consequently, considering that the action potential of the ischemic cells, upon the acute stage, has an absolute value lower than that of the same cells when properly oxigenated, if the mass of the ischemic myocardium becomes depolarized during the rising segment of the corresponding QRS complex, the values of the rising segment will result lower than those of the basic profile. If, instead, the mass becomes depolarized during the descending RS segment of the QRS complex, a raising of the profile in this segment will take place. Accordingly, the profile of the bilaterally normalized ischemic QRS complex cannot be above the one of the basic QRS in the ascending segment QR, nor below it in the descending segment RS. The occurrence of such physiologic condition is a requisite to be necessarily met and it is a criterium taken up for the alignment of the two QRS complexes overlapped for their comparison, according to the operating method of the present invention. The variation in the waveform of the normalized ischemic QRS, with respect to that of the basic QRS is characterized, instant by instant, by the difference between the two profiles (QRS1−QRS2n) the observation of which makes possible to detect also the instants of the cardiac depolarization cycle on which the major variations take place. As described later on, by referring in particular to FIGS. 3, 4 and 5, the detection of the instant in which said variations in the waveform take place allows, in turn, to localize the ischemic areas of the myocardium. Further ischemia-indicative parameters, however related to the waveform changes of the normalized ischemic QRS, may be for example: variations of the area of the QRS complexes, variation in the ratio of the semiareas subtended by the two segments of the curve QRS, variations of the derivatives at preset points of the curve QRS. Shown in the lower left side section of FIGS. 3–5 of the attached drawings are two basic QRS complexes recorded with the patient at rest, while the higher section reports their difference. The purpose of this comparison is to check for the correct acquisition of data: the two graphs shown in said higher section must result exactly superimposable, and the graph of their difference must lie around, that is close to the zero line. Shown in the lower right side section of the figures is the superimposition of the two graphs, wherein the second, that is the normalized QRS2, is recorded with the patient under stress or subject to pharmacological stimulation. The graph shown on top refers to the difference between the two QRS complexes represented in the lower section. The difference curve on the right side is related to a scale having intervals of 10 msec, to allow for an immediate evaluation of any variation in the normalized QRS2 with respect to the basic QRS. Also reported on this graph are two horizontal lines (x, y) lying on opposite sides with respect to the zero line and representing the normality threshold which, according to medical case histories, may be fixed to 3% of the maximum normalized QRS. In this way, as indicated above, it is possible to display any variation in the waveform of the ischemic QRS with respect to the basic QRS, as well as the instant at which the maximum deviation from the beginning of the cardiac depolarization cycle takes place, and the amplitude of the same variation. Experimental tests have been carried out on normal patients, and on patients suffering from inferior apical or posterolateral ischemia. In the normal subjects, the QRS monitored under stress has not revealed significant variation in the waveform with respect to the basic QRS (FIG. 3). In case of patients suffering from inferior apical ischemia, instead, a noticeable variation in the waveform has been recorded, with its peak being located within the first 35 msec (QR segment) (FIG. 4). Finally, in the case of patients suffering from lateral or posterolateral ischemia, in addition to the waveform variation in the QRS being monitored under stress, with respect to the basic QRS, the maximum of such variation has been recorded beyond the 50 msec value (RS interval) (FIG. 5). Accordingly, the assessment of the times and positions of the maximum deviations of under-stress QRS, with respect to the basic QRS, makes possible to locate the ischemic areas of the myocardium. This is supported by the maps of excitation propagation of the ventricular mass, according to which, upon the first instants the depolarization of the heart septum, apex and anterior wall occurs, while the last areas to be subjected to the depolarization are the basal and posterolateral ones.

The above described method allows results to be obtained which currently require bloody and/or costly operations and the application of highly sophisticated test techniques, such as the thallium cardiac scintigraphy, computerized axial tomography and coronarography.

Figure 2:
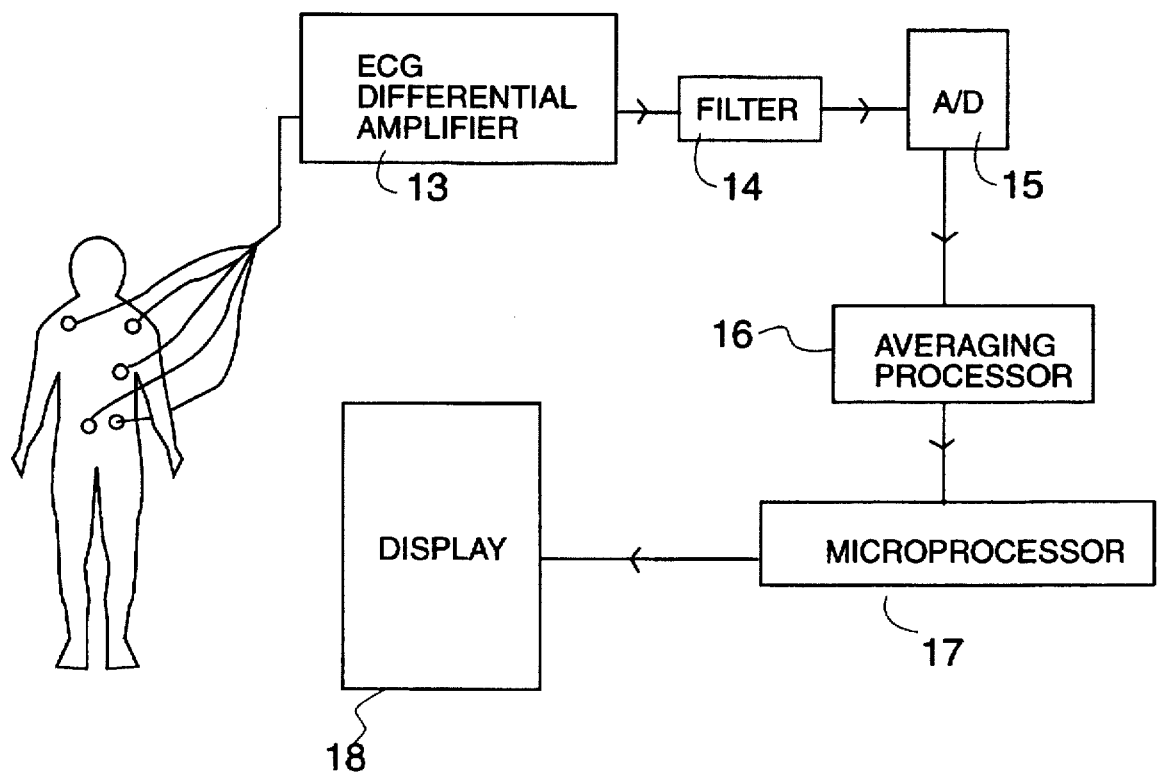
FIG. 2 shows the block diagram of an apparatus according to the invention.

As for the apparatus necessary to implement the above method, it comprises (see FIG. 2):

an ECG differential amplifier (13) connected to the thorax of the subject under test through one or more electrocardiographic leads for picking up one or more electrocardiographic signals;

a device (14) located downstream of said amplifier (13) with two active filters of second order, the first being a high-pass filter for the stabilization of the baseline of the electrocardiographic waveform, and the second a low-pass filter for minimizing accidental noises due to muscular tremor;

a 12-bit analog-digital converter (15) located downstream of said filters (14) for converting said electrocardiographic signals (for example with a conversion rate of 1000 samplings per seconds and a conversion sensitivity of 1 microV per level;

a preprocessor (16) located downstream of said converter (15) for acquiring electrocardiographic signals and making the averaging thereof;

a programmable microprocessor central unit (17) located downstream of said preprocessor (16) for automatically carrying out the operations for detecting the characteristic points (for example, minimum and maximum values) of said QRS curves, for the comparison thereof, for determining said normalization factors and for said normalizations;

a monitor and a graphic printer (18) connected to the central unit (17) for displaying and printing the waveforms of the thus processed signals. Advantageously, provision is made for the sampling rate of said converter (15) to take up a minimum value of 250 cps [cycles per second ].

Moreover, according to the invention, the conversion sensitivity of the converter (15) may be made to vary but never exceed 10 microV per level. Practically, all the construction details may vary in any equivalent way as far as the shape, dimensions, elements disposition, nature of the used materials are concerned, without nevertheless departing from the scope of the adopted solution idea and, thereby, remaining within the limits of the protection granted to the present patent for industrial invention.

We claim:

1. A method of acquiring and processing electrocardiographic signals, the method comprising the steps of:

detecting and recording a first basic electrocardiographic waveform of a subject tested under a relaxed condition;

detecting and recording a second electrocardiographic waveform of the subject tested at an end of an induced stress;

comparing said first electrocardiographic waveform with said second electrocardiographic waveform;

detecting a point in time when said second waveform differs from said first waveform by evaluating a time elapsed from a preset initial time.

2. A method in accordance with claim 1, wherein:

said point in time is a starting point of a cycle of a respective depolarization process.

3. A method in accordance with claim 1, wherein:

said point in time corresponds to a minimum value of one of said first and second waveforms.

4. A method in accordance with claim 1, wherein:

said point in time corresponds to a tangent point of one of said first and second waveforms where a local tangent is greater than a preset threshold value of a respective rising or descending segment.

5. A method in accordance with claim 1, further comprising;

determining a first averaged basic QRS from said first electrocardiographic waveform, said first averaged QRS including a first ascending segment QR and a first descending segment RS;

determining a second averaged QRS of said second electrocardiographic waveform, said second averaged QRS including a second ascending segment QR and a second descending segment RS;

detecting a first maximum R1 of said first averaged QRS;

determining a first left minimum Q1 at a left side of said first maximum R1;

determining a first left difference G1B between said first maximum and said first left minimum, G1b=R1−Q1;

detecting a first right minimum S1 at a right side of said first maximum R1;

determining a first right difference G2B between said first maximum and said first right minimum, G2b=R1−S1;

detecting a second maximum R2 of said second averaged QRS;

detecting a second left minimum Q2 at a left side of said second maximum;

determining a second left difference between said second maximum and said second left minimum G1s=R2−Q2;

detecting a second right minimum S2 at a right side of said second maximum Q2;

determining a second right difference G2s between said second maximum and said second right minimum, G2s=R2−S2;

determining a first normalization factor f1 of said RS segment and a second normalization factor f2 of said QR segment of said second averaged QRS, said first normalization factor f1 being determined by a ratio between said first right difference G2b and said second right difference G2s, said second normalization factor f2 being determined by a ratio between said first left difference G1b and said second left difference G1s;

normalizing said second segment RS of said second averaged QRS by said first normalization factor f1;

normalizing said second segment QR of said second averaged QRS by said second normalization factor f2;

connecting said normalized segments QR and RS of said second averaged QRS so as to attain a corresponding averaged QRS bilaterally normalized, QRS2n;

aligning said normalized averaged QRS, QRS2n, with said first averaged QRS to cause points of said rising QR segment of said second QRS under stress to not be above said rising QR segment of said first basic QRS, said aligning also being performed to cause points of said descending RS segment for said second QRS under stress to not be below said descending segment RS of said first QRS waveform;

detecting an alignment difference between corresponding points of said aligned normalized averaged QRS with said first averaged QRS;

plotting a graph of said alignment difference.

6. A method in accordance with claim 5, further comprising:

determining a first and a second basic mean QRS;

performing a check comparison between said first and second basic means QRS to detect errors of measurement.

7. An apparatus for acquiring and processing electrocardiographic signals, the apparatus comprising:

ECG differential amplifier means adapted to be connected to a thorax of a subject under test through one or more electrocardiographic leads, said ECG differential amplifier means picking up an electrocardiographic waveform;

filter means located downstream of said amplifier means, said filter means including a first filter being a high-pass filter for stabilization of a baseline of said electrocardiographic waveform, said filter means including a second filter being a low-pass filter for minimizing accidental noises due to muscular tremor;

an analog-digital converter means located downstream of said filter means for digitally converting said electrocardiographic waveform;

averaging preprocessor means located downstream of said converter means for acquiring said electrocardiographic waveform and forming an averaged basic QRS thereof, said averaged QRS including an ascending segment QR and a descending segment RS;

programmable microprocessor means located downstream of said averaging preprocessor means and for automatically performing the operations of:
  detecting a first normalization factor of said RS segment of said averaged QRS;
  detecting a second normalization factor of said QR segment of said averaged QRS;
  normalizing said RS and said QR segments;
  connecting said normalized segments QR and RS to attain a corresponding averaged QRS bilaterally normalized, QRS2n;
  aligning said normalized averaged QRS with another averaged QRS;
  detecting an alignment difference between corresponding points of said aligned normalized averaged QRS with said another averaged QRS;

display means connected to said programmable microprocessor means for displaying and printing waveforms from said programmable microprocessor means.

8. A method in accordance with claim 7, wherein:

said first and second filters are active filters of second order.

9. A method in accordance with claim 7, wherein:

said analog-digital converter means has a conversion rate of at least 250 samplings per second.

10. A method in accordance with claim 7, wherein:

said analog-digital converter means has a conversion sensitivity not higher than 10 microV per level.

* * * * *

UNITED STATES PATENT AND TRADEMARK OFFICE
CERTIFICATE OF CORRECTION

PATENT NO. : 5,701,906
DATED : December 30, 1997
INVENTOR(S) : ALCIDI et al.

It is certified that error appears in the above-indentified patent and that said Letters Patent is hereby corrected as shown below:

On the title page,
  [30]    Foreign Application Priority Data

May 22, 1995   [IT]  Italy ............... FI95A111

Signed and Sealed this

Twenty-eighth Day of April, 1998

Attest:

BRUCE LEHMAN

Attesting Officer

Commissioner of Patents and Trademarks